United States Patent [19]
Atkinson et al.

[11] 4,301,032
[45] Nov. 17, 1981

[54] THORIUM OXIDE-CONTAINING CATALYST AND METHOD OF PREPARING SAME

[75] Inventors: Gary B. Atkinson, Reno; Larry J. Nicks, Fernley; Donald J. Bauer, Reno, all of Nev.

[73] Assignee: The United States of America as represented by the Secretary of the Interior, Washington, D.C.

[21] Appl. No.: 152,211

[22] Filed: May 21, 1980

[51] Int. Cl.³ .......................... B01J 23/12; B01J 23/74
[52] U.S. Cl. .................................... 252/443; 252/472; 148/16
[58] Field of Search .................. 252/443, 472; 148/16

[56] References Cited
U.S. PATENT DOCUMENTS

| | | | |
|---|---|---|---|
| 2,406,172 | 8/1946 | Smithells | 252/472 X |
| 4,071,473 | 1/1978 | Atkinson et al. | 252/466 J |
| 4,203,870 | 5/1980 | Nielsen | 252/472 X |

*Primary Examiner*—W. J. Shine
*Attorney, Agent, or Firm*—William S. Brown; Donald A. Gardiner

[57] ABSTRACT

An alloy of thorium and a Group VIII transition metal is oxidized, for example in air, and subsequently reduced, for example with hydrogen gas, to produce a high surface area catalyst containing thorium oxide and one or more Group VIII transition metals. The catalyst thus produced may be used as such or may be further treated to enhance its activity.

14 Claims, No Drawings

THORIUM OXIDE-CONTAINING CATALYST AND METHOD OF PREPARING SAME

BACKGROUND OF THE INVENTION

This invention relates to a catalyst containing thorium oxide and at least one Group VIII transition metal, such as nickel, cobalt or iron thorium oxide.

The transition metals of Group VIII of the Periodic Table have long been known for their catalytic activity when prepared in a finely divided or high surface area form. Nickel in particular has found extensive use as a catalyst in hydrogenation and methanation reactions. A number of standard techniques to obtain high surface area metal catalysts have been developed. Illustrative of these are impregnation, precipitation, ion-exchange, Raney metal and reduction of the fused oxide. Since reactions which are promoted with a catalyst usually occur on the surface of the catalyst through adsorption of one or more of the reactants, it is usually desirable to obtain catalysts with the largest active surface area practicable.

Another technique which is useful to prepare catalysts from an alloy of a Group VIII transition metal and yttrium or a rare earth metal is described in U.S. Pat. No. 4,071,473, issued on Jan. 31, 1978. This process includes an activation step which involves further treatment of a material prepared by treating an alloy at elevated temperature in a hydrogen-carbon monoxide gas mixture. In the further treatment step the same reactive gas mixture may be used but at a lower temperature. The disclosure of U.S. Pat. No. 4,071,473 is herein incorporated by reference. That process has further been extended to metals other than yttrium and rare earth metals as disclosed in our co-pending application Ser. No. 162,542, filed June 24, 1980, the disclosure of which is hereby incorporated by reference. While the process just referred to produces an excellent catalyst, it has now been found that a catalyst of thorium oxide and at least one Group VIII transition metal can be prepared from an alloy by a simple oxidation procedure in air followed by reduction of the transition metal oxide.

SUMMARY OF THE INVENTION

A high surface area, thorium oxide-containing catalyst is prepared by providing an alloy of thorium and at least one Group VIII transition metal, oxidizing the alloy in an oxidizing atmosphere to oxidize the thorium, and treating the oxidized material in a reducing atmosphere to reduce transition metal oxide to free metal to produce a catalyst comprising at least one Group VIII transition metal and thorium oxide.

DETAILED DESCRIPTION OF THE INVENTION

The alloy which is useful in the present invention can be made in any convenient manner such as by arc melting in an inert atmosphere. The alloy contains thorium and any one or more of the transition metals of Group VIII of the Periodic Table. Alloy composition is not critical. A broad range of the two components can be used to produce useful catalysts. Alloy composition may usefully range from 5% to about 95% by weight of the transition metal component with the balance being made up of thorium. More preferred compositions range from about 10% to about 80% by weight of the transition metal component. Any one of the Group VIII transition metals, iron, cobalt, or nickel, may be used as the first alloy component, but nickel is preferred because of its generally higher catalytic activity. These metals may be also used in combination.

The alloy material is preferably processed in particulate form. If the alloy is provided initially in bulk, it can be readily reduced to convenient particle size by conventional crushing and grinding equipment. In general, a particle size of at least minus 10 mesh down to 200 mesh will be suitable.

The oxidizing atmosphere preferably comprises air. Air containing water vapor is suitable. Oxidation of the alloy is carried out at a temperature suitable to effect oxidation of the thorium and generally within the range of 300° to 600° C. A range of 350° to 550° C. is preferred. Pressure is not critical but a pressure of at least atmospheric is desired to reduce reaction time. Pressures of up to 60 atmospheres and above are quite suitable. Reaction time is that which is needed to effect oxidation of the thorium and this will in turn depend on other factors including the size of the alloy particles, temperature and pressure.

After oxidation, the material is treated under conditions which will reduce the oxide of the Group VIII transition metal without reducing the thorium oxide. Since the thorium oxide is extremely resistant to reduction, this can be readily accomplished under conventional reducing conditions such as treatment with hydrogen gas at elevated temperature. The temperature during reduction is generally about the same as that during oxidation and preferably about 350° to 550° C. Pressure is not critical and, as in the case of oxidation, is conveniently from atmospheric up to 60 or 100 atmospheres. The time required for reduction of the Group VIII metal oxide is generally less than required for oxidation and will depend on variables such as particle size, temperature and pressure.

The product resulting from the oxidation step includes thorium oxide and an oxide of the Group VIII transition metal. After reduction, the product is a high surface area catalyst useful for methanation and containing thorium oxide and the Group VIII transition metal.

While it is not necessary to do so, the catalyst thus produced may be further treated by carburization to increase its activity. This is accomplished by reacting the catalyst with a carburizing reagent under suitable conditions to effect formation of a carbide of the Group VIII transition metal. Carburization may be effected with a reactive gas containing hydrogen and carbon monoxide. The reactive gas may be a mixture containing only hydrogen and carbon monoxide or it may be in admixture with other gases, including steam, carbon dioxide, lower hydrocarbons such as methane and similar gases. Inert diluent gases such as helium may also be used in the gas mixture. When the catalyst is to be used in methanation reactions, synthesis gas is preferred as the activating agent as it is readily available and produces entirely satisfactory results. Reaction temperature for the carburization reaction is generally lower than that use of oxidation and reduction, generally below 275° C. and preferably below 250° C.

After carburization, the catalyst contains thorium oxide and a carbide of the Group VIII transition metal. The carbon can be removed prior to use of the catalyst by any suitable means such as by treatment with a reducing gas such as hydrogen.

EXAMPLE 1

An alloy containing 44.1 weight % thorium and 55.9 weight % nickel is prepared by arc melting the components on a water cooled copper hearth in a helium atmosphere. The alloy is then ground to minus 25 to plus 80 mesh size. Eight grams of the alloy is then treated with flowing air at a temperature of about 400°–450° C. for 48 hours. X-ray diffraction of the material after the air oxidation treatment indicates the presence of $ThO_2$, NiO and nickel metal. A one-half inch outside diameter stainless steel tube reactor is loaded with 6.43 grams of the oxidized material and flushed with helium while being heated to 400° C. When the sample temperature reaches 400° C., the helium is replaced with hydrogen for two hours to reduce the nickel metal. The product is an excellent catalyst having a BET area of 46.6 $m^2/g$ and an active area of 23.0 $m^2/g$.

EXAMPLE 2

Example 1 is followed except that after reduction with hydrogen for two hours, the sample temperature is reduced to 175° C. and the hydrogen is replaced with a mixture of 75 volume % $H_2$ and 25 volume % CO at 10 atmospheres and a flow of 67 cc per minute overnight. The product is an excellent catalyst having a BET area of 53.2 $m^2/g$ and an active area of 38.2 $m^2/g$. X-ray diffraction data indicates the presence of $ThO_2$, $Ni_3C$, and nickel. Carbon content is 2.6% by weight. Methanation activity data shows the activity of the catalyst expressed as a turnover number (molecule $CH_4$/sec/sute) is 4.3 at 225° C.

What is claimed is:

1. A method of producing a thorium oxide-containing catalyst comprising:

providing an alloy of thorium metal and at least one metal from the group consisting of nickel, cobalt and iron;

oxidizing said alloy in an oxidizing atmosphere to oxidize said metals; and treating the oxidized material in a reducing atmosphere to reduce oxides of nickel, cobalt or iron to free metal to produce a catalyst containing thorium oxide and at least one metal from the group consisting of nickel, cobalt and iron.

2. A method according to claim 1 wherein said oxidizing atmosphere comprises air.

3. A method according to claim 2 wherein said atmosphere comprises water vapor.

4. A method according to claim 1 wherein the alloy is oxidized at a temperature of about 350° to 550° C.

5. A method according to claim 1 wherein the amount of thorium in said alloy is about 5–95% by weight based on the weight of the alloy.

6. A method according to claim 1 wherein the oxidized alloy is reduced at a temperature of about 350° to 550° C.

7. A method according to claim 1 comprising the further step of reacting said catalyst with a carburizing reagent at a temperature sufficiently high and for a temperature sufficiently long to produce a catalyst comprising thorium oxide and a carbide of said nickel, cobalt or iron.

8. A method according to claim 7 wherein said carburizing reagent comprises a mixture of carbon monoxide and hydrogen.

9. A method according to claim 8 wherein said temperature is below about 250° C.

10. A method according to claim 7 comprising the further step of removing carbon from the carbide-containing catalyst.

11. A method according to claim 10 wherein carbon removal is effected by treating the carbide-containing catalyst with a reducing gas.

12. A catalyst produced by the process of claim 1.

13. A catalyst produced by the process of claim 7.

14. A catalyst produced by the process of claim 10.

* * * * *